United States Patent
Ohkubo et al.

(10) Patent No.: US 8,218,883 B2
(45) Date of Patent: Jul. 10, 2012

(54) IMAGE COMPRESSION METHOD, IMAGE COMPRESSION DEVICE, AND MEDICAL NETWORK SYSTEM

(75) Inventors: Takeshi Ohkubo, Kanagawa (JP); Hideyuki Sakaida, Tokyo (JP)

(73) Assignee: Fujifilm Corporation, Tokyo (JP)

( * ) Notice: Subject to any disclaimer, the term of this patent is extended or adjusted under 35 U.S.C. 154(b) by 656 days.

(21) Appl. No.: 12/443,025

(22) PCT Filed: Sep. 21, 2007

(86) PCT No.: PCT/JP2007/068346
§ 371 (c)(1),
(2), (4) Date: Mar. 26, 2009

(87) PCT Pub. No.: WO2008/038581
PCT Pub. Date: Apr. 3, 2008

(65) Prior Publication Data
US 2010/0074484 A1   Mar. 25, 2010

(30) Foreign Application Priority Data
Sep. 27, 2006  (JP) ................. 2006-262103

(51) Int. Cl.
*G06K 9/00* (2006.01)
*G06K 9/36* (2006.01)
*G06K 9/46* (2006.01)
(52) U.S. Cl. .................. 382/232; 382/239; 382/128
(58) Field of Classification Search ............... None
See application file for complete search history.

(56) References Cited

U.S. PATENT DOCUMENTS 6,144,772 A * 11/2000 Garland et al. ............... 382/239
7,327,866 B2 * 2/2008 Bae et al. ...................... 382/131
(Continued)

FOREIGN PATENT DOCUMENTS

EP          1 229 457          8/2002
(Continued)

OTHER PUBLICATIONS

"Monthly Innervision", published by Kabushiki Kaisha Innervision, Apr. 2005, extra edition. vol. 20, No. 5 (Consecutive No. 229), p. 182-187.

*Primary Examiner* — Li Liu
(74) *Attorney, Agent, or Firm* — Young & Thompson (57) ABSTRACT

Volume data (32) constituted of more than one slice image (30) shot with a CT scanner (12) is transferred to an image server (14). A CPU (40) of the image server (14) makes a site recognizing section (46) recognize a site of each slice image (30) included in the volume data (32). The recognized site is recorded in a tag area (36) of each slice image (30) as site information (36c). The CPU (40) refers to the site information (36c) of each slice image (30) and judges whether more than one site is included in the volume data (32) or not. When judging that more than one site is included in the volume data (32), an image compression section (47) selects a common compression mode and compresses each slice image (30) under a common compression format and a common compression ratio.

10 Claims, 10 Drawing Sheets

U.S. PATENT DOCUMENTS

| | | | |
|---|---|---|---|
| 7,548,657 B2 * | 6/2009 | Deaven | 382/243 |
| 2002/0090140 A1 * | 7/2002 | Thirsk | 382/239 |
| 2002/0102028 A1 | 8/2002 | Keller et al. | |
| 2004/0022447 A1 * | 2/2004 | Mukhopadhyay et al. | 382/243 |
| 2006/0171578 A1 * | 8/2006 | Novak | 382/131 |
| 2007/0065032 A1 * | 3/2007 | Hernandez et al. | 382/239 |
| 2007/0127790 A1 * | 6/2007 | Lau et al. | 382/128 |
| 2007/0269089 A1 * | 11/2007 | Sakaida | 382/128 |
| 2007/0269117 A1 * | 11/2007 | Ernvik et al. | 382/232 |
| 2008/0037714 A1 * | 2/2008 | Sakaida et al. | 378/207 |
| 2008/0037849 A1 * | 2/2008 | Sakaida et al. | 382/131 |

FOREIGN PATENT DOCUMENTS

| | | |
|---|---|---|
| JP | 2002-282247 | 10/2002 |
| JP | 2002-352220 | 12/2002 |
| JP | 2002-360521 | 12/2002 |
| JP | 2005-34473 | 2/2005 |
| JP | 2005-287927 | 10/2005 |
| JP | 2006-180987 | 7/2006 |

* cited by examiner

IMAGE COMPRESSION METHOD, IMAGE COMPRESSION DEVICE, AND MEDICAL NETWORK SYSTEM

TECHNICAL FIELD

The present invention relates to an image compression method for selecting one of a site-specific compression mode in which a compression format and a compression ratio vary depending on an anatomical site and a common compression mode in which a compression format and a compression ratio are common regardless of the anatomical site and performing compression under the selected mode over an image group composed of a plurality of slice images obtained using a modality, and an image compression device and a medical network system using this method.

BACKGROUND ART

In medical facilities like clinics and hospitals, a variety of modalities, such as devices for CR (computed radiography), CT (computed tomography), MRI (magnetic resonance imaging), PET (positron emission tomography) and ultrasonic diagnosis, have been widely used. Medical images shot by the modalities are used in medical diagnoses, taking an important roll when doctors determine the symptoms of patients.

The medical images are stored in the medical facilities for several years since it is obliged to store them for a certain period of time or they need to be referred for a follow-up. The medical facilities therefore need to store a large amount of medical images. If each medical image is stored in the form of film, a storage space becomes huge, and management and search thereof becomes a heavy burden. To avoid such situation, for example, a diagnosis support system of Japanese Patent Laid-Open Publication No. 2002-282247 digitizes medical images and stores them in a sever and the like. According to this system, the medical facilities need only to prepare the space for the server, and thus the storage space for the medical images can be significantly reduced. In, addition, when the management and the search of the medical images are performed by the server, work performance in the medical facilities can be improved.

By the way, since the stored medical images cannot easily be deleted, a server of such medical system needs to expand its recording capacity when it becomes full. However, the expansion of storage capacity costs a lot. In view of this, compression is often performed to each medical image and thereby reducing consumption of the recording capacity in the server (for example, see Japanese Patent Laid-Open Publication No. 2002-282247).

For the compression, there are lossless compression and lossy compression. In the lossless compression, the image quality is not lost, however it is difficult to drastically reduce the consumption of the recording capacity since the compression ratio is low. Meanwhile, in the lossy compression, although the compression ratio is high, it also involves the image quality loss, and therefore it may cause misdiagnosis.

In view of this, for the lossy compression, a server which effectively reduces the consumption of the recording capacity, while maintaining the image quality, by setting an appropriate compression ratio for each site, such as head or chest, is developed. (For example, see "monthly INNERVISION", published by Kabushiki Kaisha Innervision, April 2005, extra edition, Volume 20, Number 5 (Consecutive Number 229), p. 182-187). This server uses the theory that the degree of image quality loss varies depending on the site being shot. For example, an image precisely showing a picture of air area and bone area (or blood vessels and bronchial tubes) has high contrast, and therefore the image quality loss becomes distinctive when the compression ratio is high. Meanwhile, an image of neck or abdomen has few area of high contrast, and therefore the image quality loss becomes less distinctive even when the compression ratio is high. Accordingly, low compression ratio is applied for the head or chest, whereas high compression ratio is applied for the neck and abdomen, and thereby the consumption of the recording capacity can effectively be reduced while maintaining the constant image quality.

Medical images shot with the CT scanner or the MRI scanner are slice images capturing cross section of a human body. When using the CT scanner or the MRI scanner, a plurality of slice images shot from different positions are normally obtained in a single examination. In addition, it has recently been possible to shoot across all sites which may be objected for examination at one time owing to improvement in shooting capability of each modality. A group of the shot slice images is classified by site and then stored or transferred to each specialist.

In the event the slice images classified by site are interpreted, some of the adjacent slice images also need to be observed if a lesion is found near the boundary of the sites. In the case that the contrast ratio has been changed from site to site as described above, however, the image quality may drastically change between the adjacent sites like for example the chest and the abdomen, which causes difficulty in the interpretation. Especially when the lesion resigns across the adjacent sites, it is hard to distinguish between the change due to the lesion and the change due to the image quality loss, and it may cause misdiagnosis.

It is an object of the present invention to provide an image compression method, an image compression device, and a medical network system capable of effectively reducing consumption of recording capacity while keeping image quality and also preventing image quality from changing between adjacent sites when storing a plurality of medical images shot in a single examination.

DISCLOSURE OF INVENTION

In order to achieve the above object, an image compression method of the present invention selects one of a site-specific compression mode and a common compression mode, owing to a judgment step and a site recognition step, and performs compression to an image group. The image group is constituted of more than one medical image shot with a modality. The site-specific compression mode uses a compression format and/or a compression ratio corresponding to an anatomical site. The common compression mode uses a common compression format and/or a common compression ratio regardless of the anatomical site. In the judgment step, it is judged whether or not more than one anatomical site is included in the image group based on site information indicating anatomical site of the medical image. In the compression step, compression under the common compression mode is performed when it is judged that more than one anatomical site is included in the image group, whereas compression under the site-specific compression mode is performed when it is judged that only one anatomical site is included in the image group.

In the site-specific compression mode, it is preferable that compression information indicating a compression format and a compression ratio for each anatomical site is referred, and the compression format and/or the compression ratio corresponding to the anatomical site is set.

In addition, it is preferable that a site recognition step for recognizing an anatomical site in the medical image by image analysis and a site information production step for producing the site information regarding each medical image based on the recognition result of the site recognition step are further provided before the judgment step.

Moreover, it is preferable that the site information is recorded in each medical image as metadata.

In addition, it is preferable that a storage step for storing the image group after the compression to a storage means is further provided. Alternatively, it is preferable that a transfer step for transferring the image group after the compression to a terminal used for a diagnosis. Moreover, the anatomical site is preferably at least one of head, neck, chest, abdomen, pelvic region and leg. In addition, the medical image is preferably a slice image capturing cross section of a human body.

An image compression device of the present invention includes a judgment means and a compression means, and selects one of a site-specific compression mode and a common compression mode and performs compression to an image group. The image group is constituted of more than one medical image shot with a modality. The site-specific compression mode uses a compression format and/or a compression ratio corresponding to an anatomical site. The common compression mode uses a common compression format and/or a common compression ratio regardless of the anatomical site. The judgment means judges whether or not more than one anatomical site is included in the image group based on site information indicating anatomical site of the medical image. The compression means performs compression under the common compression mode when it is judged that more than one anatomical site is included in the image group, whereas performing compression under the site-specific compression mode when it is judged that only one anatomical site is included in the image group.

A medical network system includes a server and a terminal connected to the server through a network. The server is provided with a storage means for storing an image group constituted of more than one medical image shot with a modality and selects one of a site-specific compression mode using a compression format and/or a compression ratio corresponding to an anatomical site and a common compression mode using a common compression format and/or a common compression ratio regardless of the anatomical site and performs compression to the image group. The image group is read out from the server to the terminal upon request from a user. In addition, the server is provided with a judgment means and a compression means. The judgment means judges whether or not more than one anatomical site is included in the image group based on site information indicating anatomical site of the medical image. The compression means performs compression under the common compression mode when it is judged that more than one anatomical site is included in the image group, whereas performing compression under the site-specific compression mode when it is judged that only one anatomical site is included in the image group.

According to the present invention, when more than one anatomical site is included in the image group, compression is performed under the common compression mode using the common compression format and/or the common compression ratio for each medical image. Therefore, the change of image quality between the adjacent anatomical sites is prevented. When only one anatomical site is included in the image group, compression is performed under the site-specific compression mode using the compression format and/or the compression ratio corresponding to the anatomical site. Therefore, the consumption of the recording capacity can be reduced while maintaining the image quality.

BRIEF DESCRIPTION OF DRAWINGS

FIG. 6 are explanatory views respectively showing an example of volume data including a plurality of sites and an example of volume data including a single site;

BEST MODE FOR CARRYING OUT THE INVENTION

Figure 1:
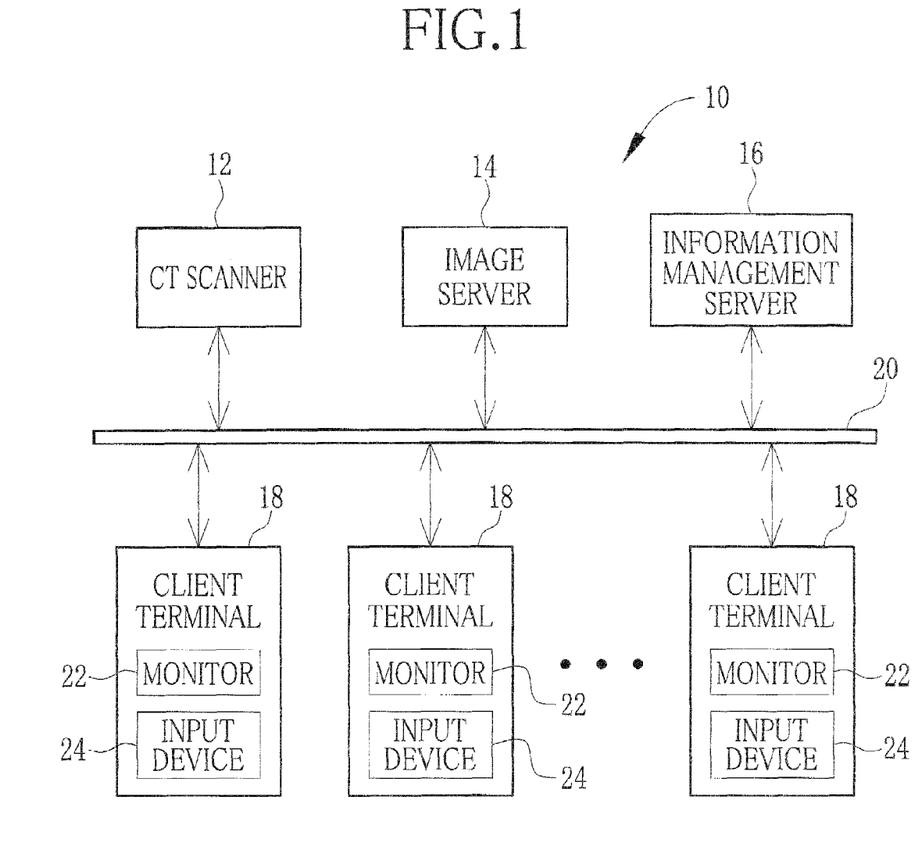
FIG. 1 is a block diagram schematically illustrating a structure of a medical network system.

FIG. 1 is a block diagram schematically illustrating a structure of a medical network system 10 used in a medical facility like a hospital. The medical network system 10 is constituted of a CT scanner (modality) 12 for shooting slice images of patients and the like as medical images, an image server (image compression device) 14 for storing the slice images shot with the CT scanner 12, an information management server 16 for managing various information inside the medical facility, and a plurality of client terminals (terminal) 18 operated by doctors during diagnoses and the like. These components are connected with each other through a LAN (network) 20 in the medical facility.

The medical network system 10 manages various information and medical images treated in the medical facility as electronic data, and thereby reducing storage space for medical records and films of medical images in the medical facility. In addition, the medical network system 10 enables each of the client terminals 18 to easily read out the various information and medical images, and thereby improving the efficiency of operations in the medical facility. Although FIG. 1 shows a plurality of client terminals 18, only one client terminal 18 may be provided in the medical network system 10. On the contrary, more than one of each CT scanner 12, image server 14, and information management server 16 may be provided in the medical network system 10.

The image server 14 is, for example, a so-called PACS (picture archiving and communication system for medical application) server. Besides the slice images from the CT scanner 12, the image server 14 stores medical images sent from other medical facilities via a network or media and reference images used for comparison of symptoms. The medical images stored in the image server 14 are individually read out to each client terminal 18 as needed and used for an interpretation by a doctor or for explanation to a patient. The medical image includes, besides the slice images shot with the CT scanner 12, images shot with other modalities like the devices for CR and MRI. In addition, the reference image includes, besides the images shot with the modalities, those drawn as illustrations.

The information management server 16 is, for example, an HIS (hospital information system) server or a RIS (radiology information system) server. The information management server 16 manages various information including patient information, diagnosis and treatment information, examination information and account information for individual patients. The patient information represents personal information of a patient such as, for example, patient's name, patient's ID, address, birthday, age, sex, family, anamnesis or past illnesses and allergies.

The diagnosis and treatment information represents information on the diagnosis and treatment made to the patient, including the date of medical session, the department in charge, the name of disorder, the result of diagnosis, the duration of therapy, the kinds and amounts of prescribed drugs, the name of pharmacy in charge of medication, etc. The duration of therapy represents how long the patient has come to the medical facility for the therapy of the same disorder. The examination information represents information on medical images shot at each examination, including the date of examination, the machine used for the examination, the method of the examination and the site under the examination, etc. The information on the method of the examination includes directions and angles of shooting the respective medical images, such as front and side, as well as whether radiopaque is used or not. The examined sites mean body regions to be examined, such as head, neck, chest region, abdominal region, pelvic region, leg, and combination thereof like head and neck regions, thoracoabdominal region, etc. The account information includes, for example, charges for medical sessions, medications and inspections as well as whether the coverage is available or not.

In the medical facility, the client terminals 18 are put in, for example, every examination room or every department. Each client terminal 18 is constituted of, for example, a well-known personal computer or work station, and includes a monitor 22 for displaying various information and medical images, an input device 24 for inputting various information, and the like. The doctor makes a diagnosis while seeing the monitor 22 displaying the slice images shot with the CT scanner 12 and the information read out from the information management server 16, or explains the result of diagnosis using the slice images displayed on the monitor 22. In addition, the doctor inputs information obtained through the session using the input device 24. Note that a well-known display device, such as a CRT display or a liquid crystal display is used as the monitor 22. In addition, well-known input devices like a keyboard and a mouse are used as the input device 24.

In the information management server 16, a reservation list of the CT scanner 12 is stored. When shooting with the CT scanner 12 is needed, the doctor accesses the reservation list in the information management server 16 from the client terminal 18. When available date in the reservation list is selected and order information instructing content of examination (examination details) is input, the examination using the CT scanner 12 is reserved. The information management server 16 sends the order information to the client terminal 18 and the CT scanner 12 in a radiologic department periodically or every time a new examination reservation is received. A Doctor or an operator of the radiologic department operates the CT scanner 12 and takes slice images according to the order information.

In this way, the information management server 16 manages information for respective patients, and also manages available status of the CT scanner 12 so that the examinations will not be overbooked in the same period of time. The order information includes, for example, the method of the examination, the site under the examination, the patient's ID, and the ID of the doctor who has requested the examination.

Figure 2:
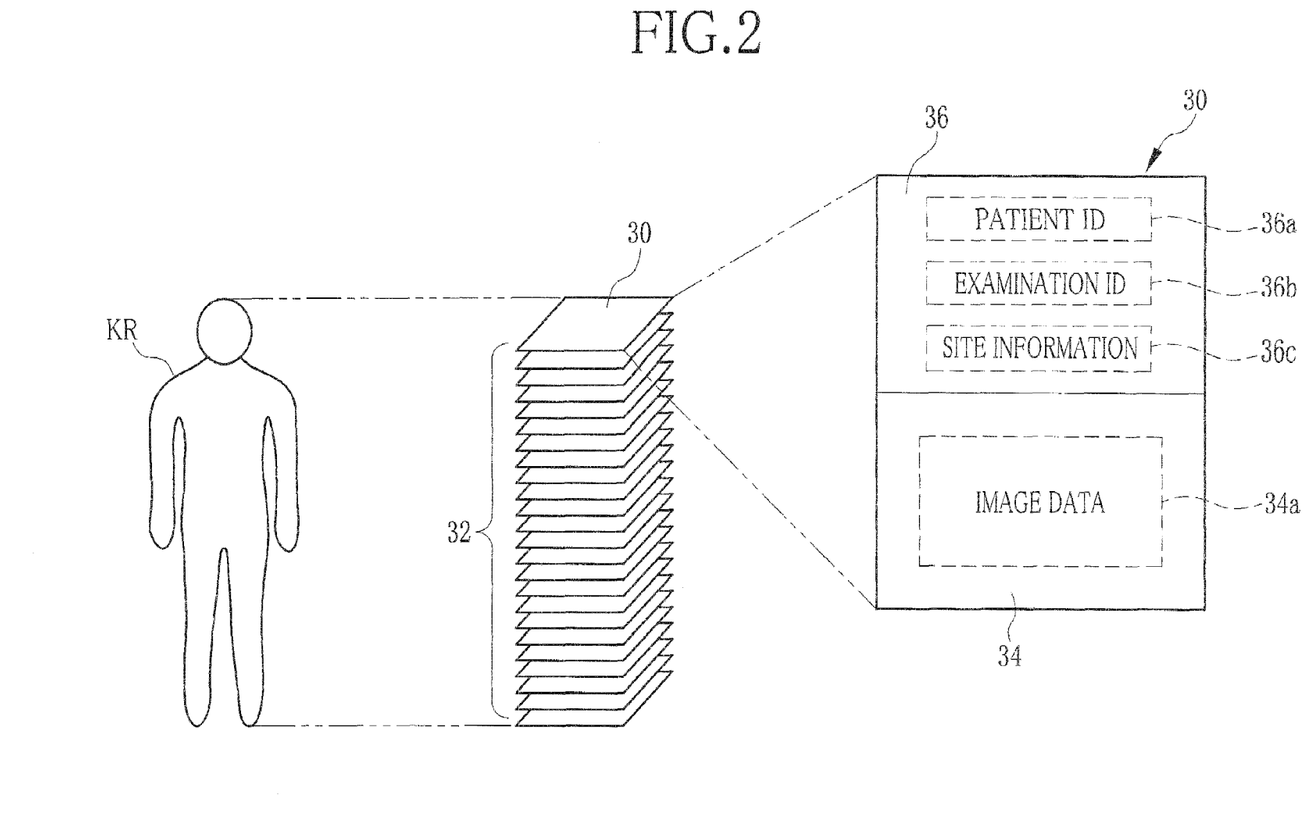
FIG. 2 is an explanatory view schematically illustrating structures of volume data and slice images.

As shown in FIG. 2, a plurality of slice images 30 is shot for one patient KR in the examination using the CT scanner 12 according to a setting of slice thickness and the like. These slice images 30 are transferred to the image server 14 and stored therein while being organized by each examination. Hereinafter, a group of the slice images obtained in a single examination is referred to as volume data (image group) 32. In addition, in the case where the volume data 32 includes more than one site, all of the sites may be shot continuously or shooting may be performed intermittently, that is, from site to site.

Each slice image 30 has an image recording area 34 for recording image data 34*a* and a tag area 36 for recording metadata. In the tag area 36, for example, a patient ID 36*a*, an examination ID 36*b*, site information 36*c* and the like are recorded. The patient ID 36*a* is used for identifying which patient KR the slice images 30 are taken from. The examination ID 36*b* is, for example, a specific number given to each examination. This examination ID 36*b* makes it possible to identify which examination the slice image 30 is shot for and used to manage each of the slice images 30 as the volume data 32.

The site information 36*c* indicates which site is shot in the slice image 30. Each of these metadata may be recorded, for example, by the CT scanner at the time of shooting the slice image 30, or recorded in the image server 14 or in the client terminal 18 after the slice image 30 has been shot. Note that the metadata is not limited to the above embodiment, but may be any other information as long as it makes the identification of each slice image 30 possible. As an example of file format for such medical image as having the tag area 36, DICOM (digital imaging and communications in medicine) format is usable.

Figure 3:
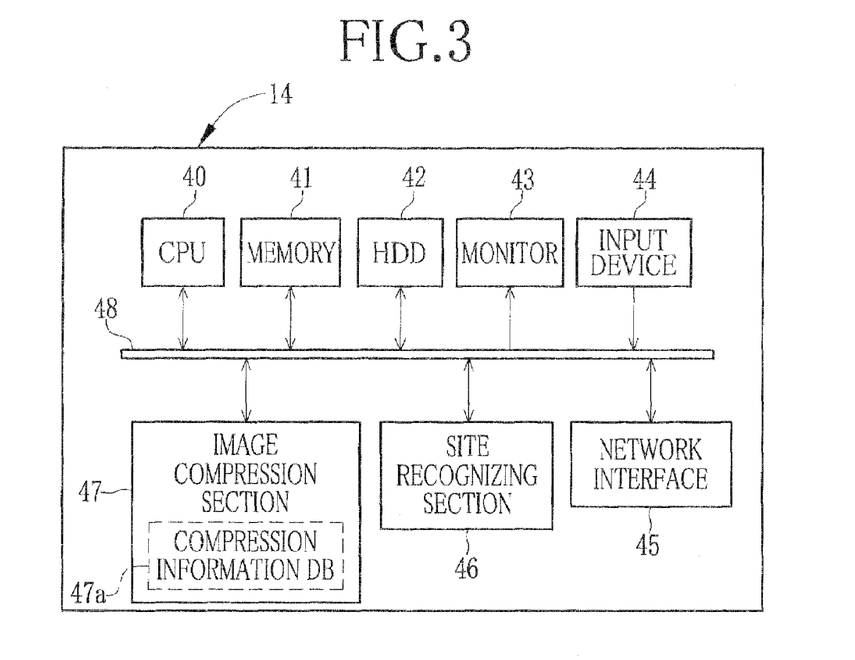
FIG. 3 is a block diagram schematically illustrating a structure of an image server.

FIG. 3 is a block diagram schematically illustrating a structure of the image server 14. The image server 14 is constituted of a well-known personal computer or work station, and includes a CPU (judgment means) 40, a memory 41, a HDD (storage means) 42, a monitor 43, an input device 44, a network interface (transfer means) 45, a site recognizing section (site recognizing means) 46, and an image compression section (image compression means) 47. These components are connected with each other through a bus 48.

In the HDD 42, various programs for the medical network system 10 and various medical images including the slice images 30 shot with the CT scanner 12 are stored. The CPU 40 reads out each program from the HDD 42 to the memory 41 and operates it, and thereby entirely controlling the image server 14. When a medical image is input through the network interface 45, this medical image is stored in a predetermined area of the HDD 42. The stored medical image is read out from the HDD 42 upon request from each client terminal 18 and transferred to the client terminal 18 which requested.

Although the various programs and the medical images are stored together in the HDD 42 in this embodiment, they can be stored in separate HDDs. In addition, although the built-in HDD 42 is used in this embodiment, for example, an external HDD or other kinds of media like DVD-ROM or CD-ROM may be used for the storage.

The monitor 43 displays various operation screens corresponding to processing of the program by the CPU 40. Note that a well-known display device, such as a crystal liquid display or a CRT display, is used as the monitor 43. The input device 44 may be constituted of a keyboard and a mouse. The monitor 43 and the input device 44 are used when an administrator in the medical facility renews the programs stored in the HDD 42 or for checking the storage status of the medical images in the HDD 42. The network interface 45 connects the image server 14 to the LAN 20 of the medical facility. The network interface 45 is Ethernet (trademark) or the like selected according to the standard of the LAN 20.

The site recognizing section 46 performs image analysis of the input slice image 30 and recognizes which site is shot. In addition, the site recognizing section 46 records the recognized site as the site information 36*c* in the tag area 36 of the slice image 30. The image analysis by the site recognizing section 46 is performed by, for example, calculating feature quantity of the image based on the CT value of each pixel and matching it to feature quantity of each site preliminarily stored. Specifically, the site recognition can be performed by, for example, comparing area ratio of CT value of each texture to the predetermined value on every slice image based on the theory that the proportion of each texture like bone or air in respective sites is about same and hardly differ among individuals.

The image compression section 47 performs lossy compression to the input slice image 30 and the like. At this time, a compression format and a compression ratio may arbitrary be set by, for example, the input device 44 or the like. The lossy compression format used by the image compression section 47 may be a well-known format, such as Wavelet format (for example, Japanese Patent Laid-Open Publication No. 2000-232366) or JPEG format.

In addition, the image compression section 47 has a site-specific compression mode in which a compression format and a compression ratio vary depending on the site being shot and a common compression mode in which a compression format and a compression ratio are common regardless of the site being shot. The image compression section 47 selects the common compression mode when the input volume data 32 includes more than one site, whereas selecting the site-specific compression mode when the input volume data 32 includes only one site.

Figure 4:
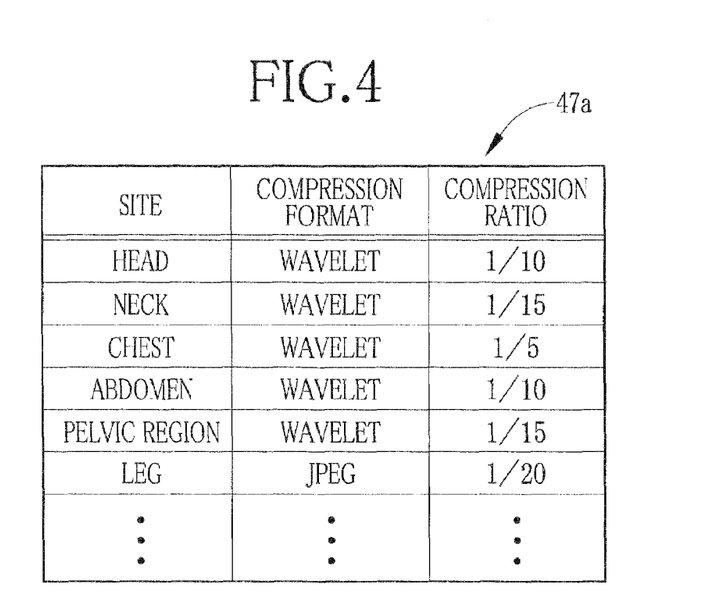
FIG. 4 is an explanatory view schematically illustrating a structure of a compression information DB.

The image compression section 47 is provided with a compression information database (DB) 47*a* used under the site-specific compression mode. In the compression information DB 47*a*, as shown in FIG. 4, the compression format and the compression ratio are indicated for each site. When performing compression under the site-specific compression mode, the image compression section 47 refers to the compression information DB 47*a* and sets the compression format and the compression ratio corresponding to the site. The compression format and the compression ratio under the common compression mode may arbitrary be set by the user, or the lowest compression ratio among the plural sites included in the volume data 32 may be selected with reference to the compression information DB 47*a*.

Figure 5:
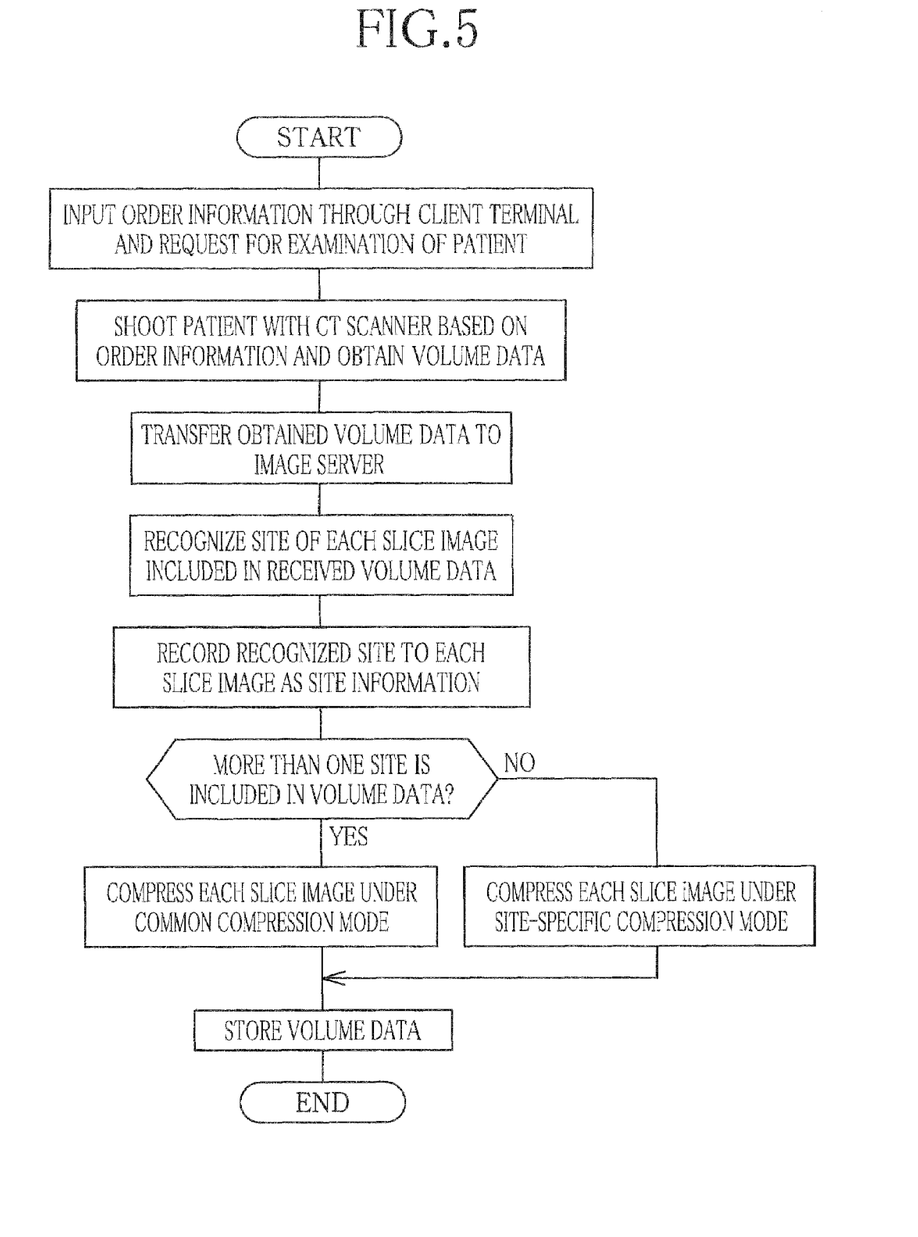
FIG. 5 is a flow chart showing an operation of the medical network system.

Now the operation of the medical network system 10 having the above configuration will be described with reference to the flow chart shown in FIG. 5. The doctor who finds it necessary to shoot images with the CT scanner 12 for a diagnosis accesses the reservation list of the information management server 16 through the client terminal 18. The doctor inputs order information on the date available in the list and thereby making reservation for examination using the CT scanner 12. The input order information is delivered from the information management server 16 to the client terminal 18 and the CT scanner 12 in the radiologic department.

The operator (radiologist or radiologic technician) of the CT scanner 12 who has checked the order information performs the shooting of the patient KR based on the order information, and obtains the volume data 32 of the site under the examination which was designated in the order information. In addition, the CT scanner 12 records the patient ID 36*a* and the examination ID 36*b* based on the order information in the tag area 36 of each slice image 30 included in the obtained volume data 32.

Regardless of the site under examination designated in the order information, it is possible to shoot a whole body of the patient KR. The volume data 32 obtained by shooting the whole body certainly includes the slice image 30 of the site which the doctor asks for. Therefore, the mismatch between the site designated in the order information and the site actually shot due to the setting failure of shooting area may be prevented.

The volume data 32 is transferred to the image server 14 through the LAN 20. The CPU 40 of the image server 14 inputs the received volume data 32 to the site recognizing section 46 and makes it recognize the site of each slice image 30 included in the volume data 32. The site recognizing section 46 records the recognized site in the tag area 36 of each slice image 30 as the site information 36*c*.

Figure 6A:
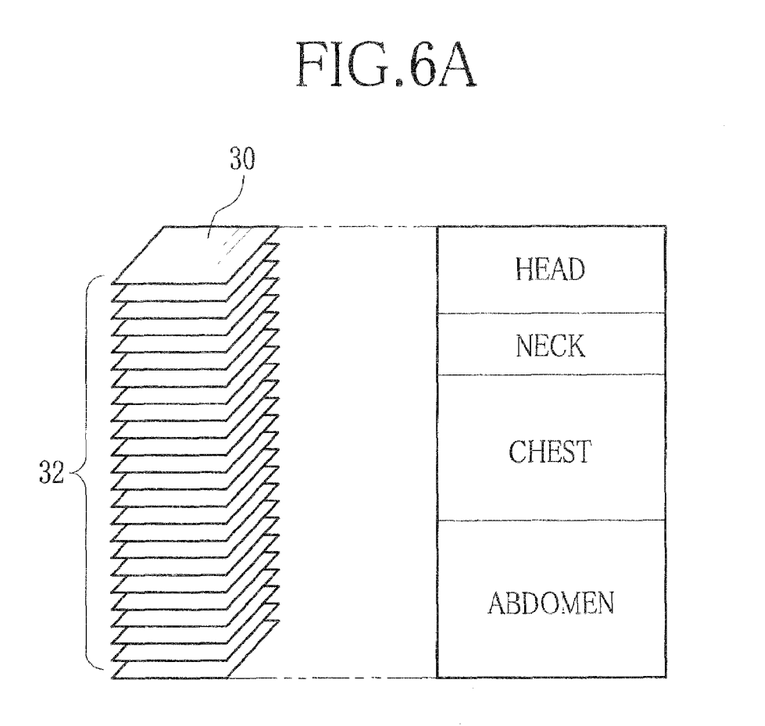

Next, the CPU 40 refers to the site information 36*c* of each slice image 30 and judges whether more than one site is included in the volume data 32 or not. The CPU 40 then inputs the judgment result and the volume data 32 to the image compression section 47. When the CPU 40 judges as the volume data 32 includes more than one site (see FIG. 6A), the image compression section 47 selects the common compression mode and performs compression to each slice image 30 under the common compression format and the common compression ratio.

Figure 6B:
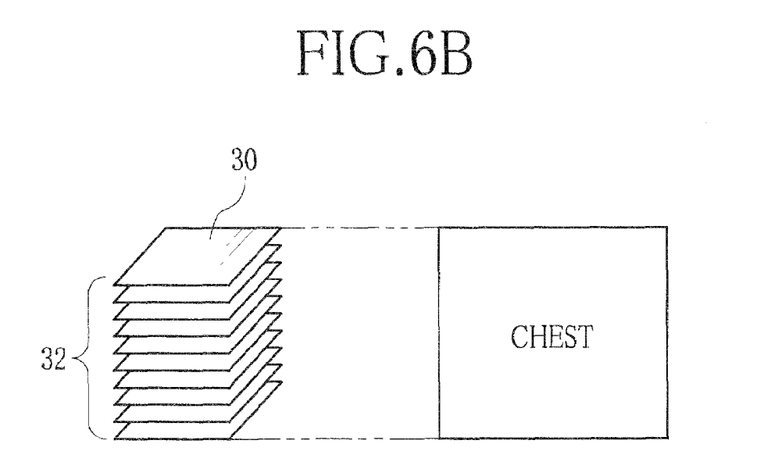

Meanwhile, when the CPU 40 judges as the volume data 32 includes only one site (see FIG. 6B), the image compression section 47 selects the site-specific compression mode. Upon selecting the site-specific compression mode, the image compression section 47 refers to the compression information DB 47*a* and performs compression under the compression format and the compression ratio corresponding to the respective slice images 30. For example, the volume data 32 shown in FIG. 6B indicates that "chest" is shot in the respective slice images 30. Accordingly, the respective slice images 30 are compressed in the "Wavelet" format with the compression ratio of "1/5" that correspond to "chest" in the compression information DB 47*a* (see FIG. 4).

After the completion of the compression by the image compression section 47, the CPU 40 stores the compressed volume data 32 to the HDD 42. As described above, common compression is performed to the plural sites included in the volume data 32 under the common compression mode. Therefore, the change of image quality between the adjacent sites is surely prevented. Under the site-specific compression mode, on the other hand, appropriate compression differ from site to site is performed. Therefore, the consumption of the recording capacity in the HDD 42 can be effectively reduced while maintaining the image quality of each slice image 30.

Figure 7:
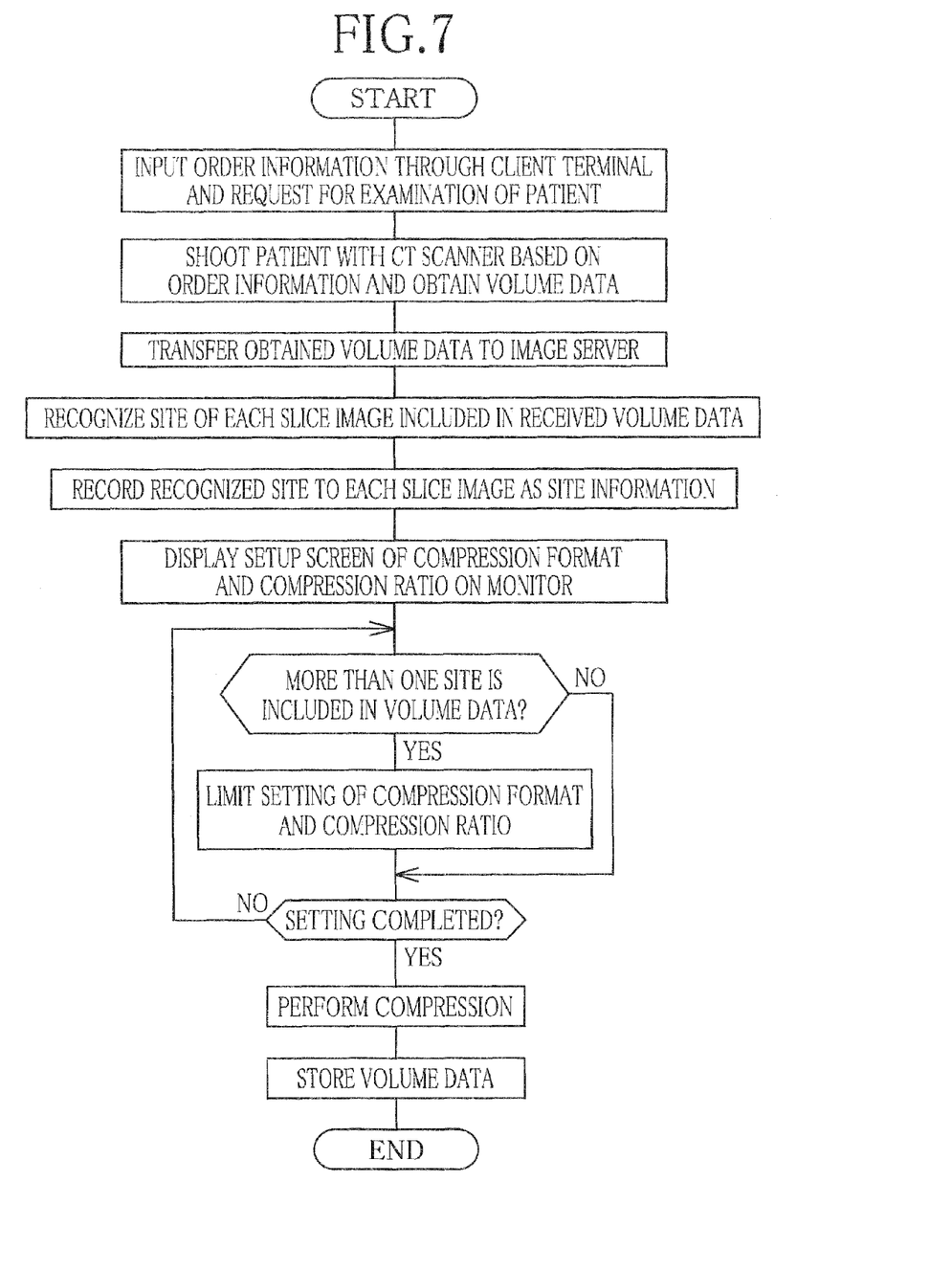
FIG. 7 is a flow chart showing procedures for manually setting a compression format and a compression ratio.

According to the above embodiment, although the image compression section 47 refers to the compression information DB 47*a*, which has preliminary been recorded, at the time of the compression and automatically sets the compression format and the compression ratio, they may be manually set by the user like the flow chart shown in FIG. 7. Note that the components same in function and configuration as those described in the above embodiment are assigned with same numerals and the explanations thereof are omitted.

Figure 8:
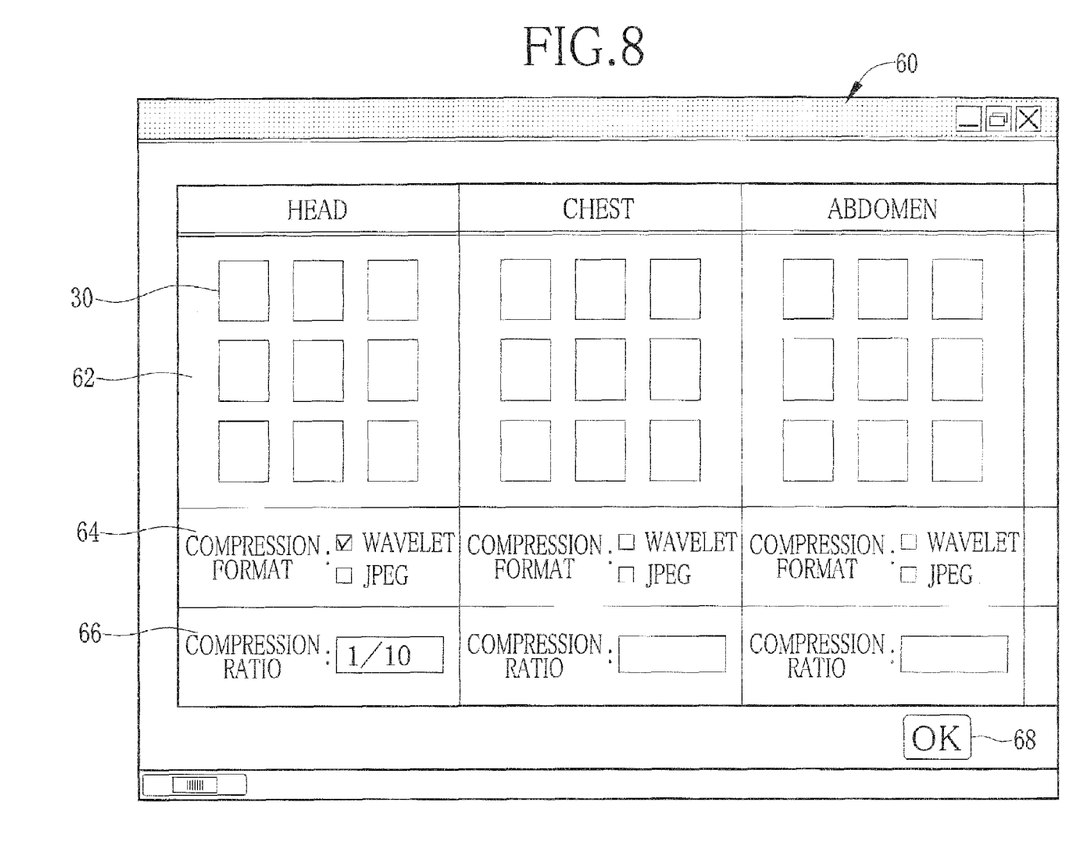
FIG. 8 is an explanatory view illustrating a setup screen.

In the flow chart shown in FIG. 7, the site recognizing section 46 is made to recognize a site of each slice image 30 and then a setup screen 60 for compression format and compression ratio shown in FIG. 8 is displayed on the monitor 43. The setup screen 60 has an image display area 62 for displaying the slice images 30, a compression format setup area 64 for setting a compression format and a compression ratio setup area 66 for setting a compression ratio, and these areas 62, 64 and 66 are provided for each site. The compression format is set by checking a check box displayed in the compression format setup area 64. In addition, the compression ratio is set by inputting any number in an input area of the compression ratio setup area 66. Moreover, the setup screen 60 is provided with an OK button 68, and the setup operation is completed by clicking this OK button 68 after setting the compression format and the compression ratio.

When the setup screen 60 is displayed on the monitor 43, the CPU 40 refers to the site information 36c of each slice image 30 and judges whether more than one site is included in the volume data 32 or not. When judging as more than one site is included in the volume data 32, the CPU 40 limits the compression format and the compression ratio displayed on the setup screen 60 so that common compression format and common compression ratio are selected for all of the sites. Owing to this, same compression is performed to the respective sites included in the volume data 32, and therefore the change of image quality between the adjacent sites is surely prevented like the above embodiment.

Figure 9:
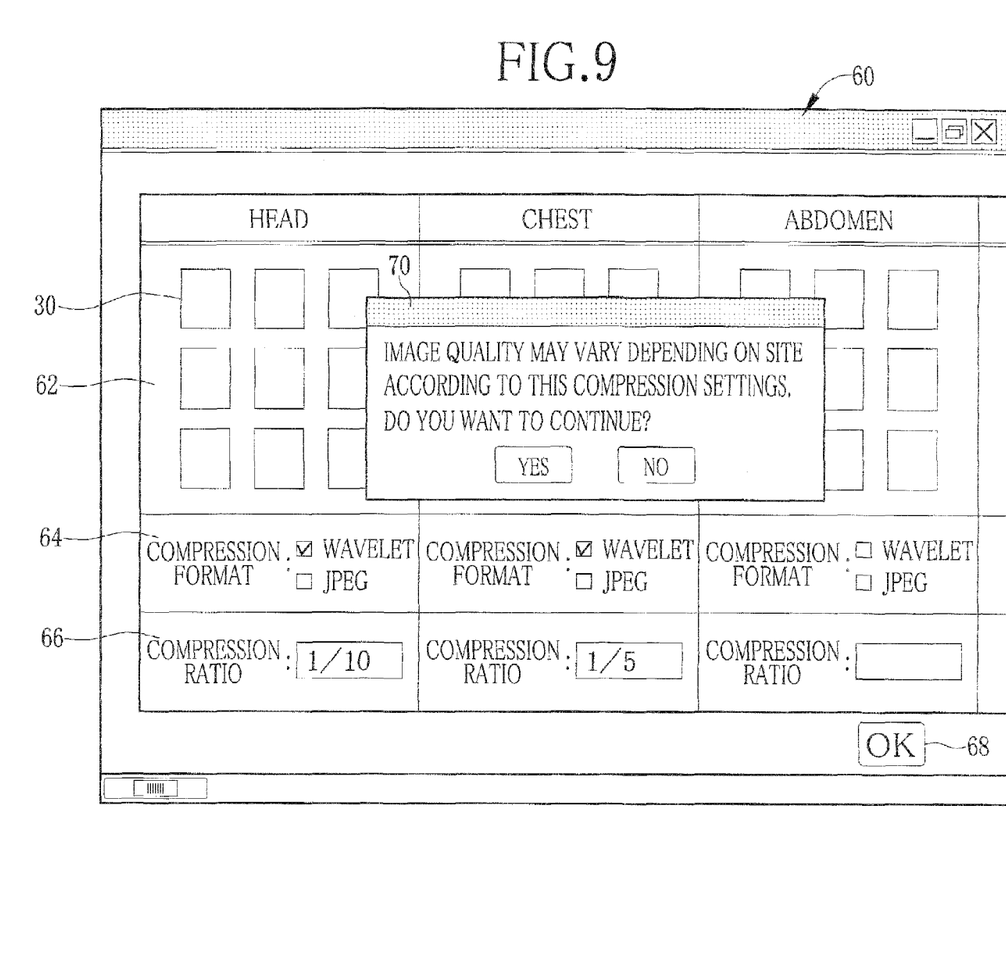
FIG. 9 is an explanatory view illustrating the setup screen with an alarm display.

Meanwhile, when judging as only one site is included in the volume data 32, the CPU 40 does not limit the setting but allows the selection of any compression format and any compression ratio. After confirming the completion of setting upon clicking the OK button 68, the CPU 40 performs compression under the compression format and the compression ratio set in the setup screen 60 to the respective slice images 30. After executing the compression, the CPU 40 stores the compressed volume data 32 to the HDD 42. When it is judged that the volume data 32 includes more than one site, a message box 70 may pop-up as shown in FIG. 9 to alert that a compression format and a compression ratio differ from site to site are selected, instead of limiting the setting. Instead of the message box 70, warning light may be lit up or warning beep may be turned on. Moreover, instead of limiting a target for alarm to specific compression format and compression ratio, it may be possible to define an acceptable range so that the limitation or the alarm is given only to the compression format and the compression ratio exceeds the allowable range.

Figure 10:
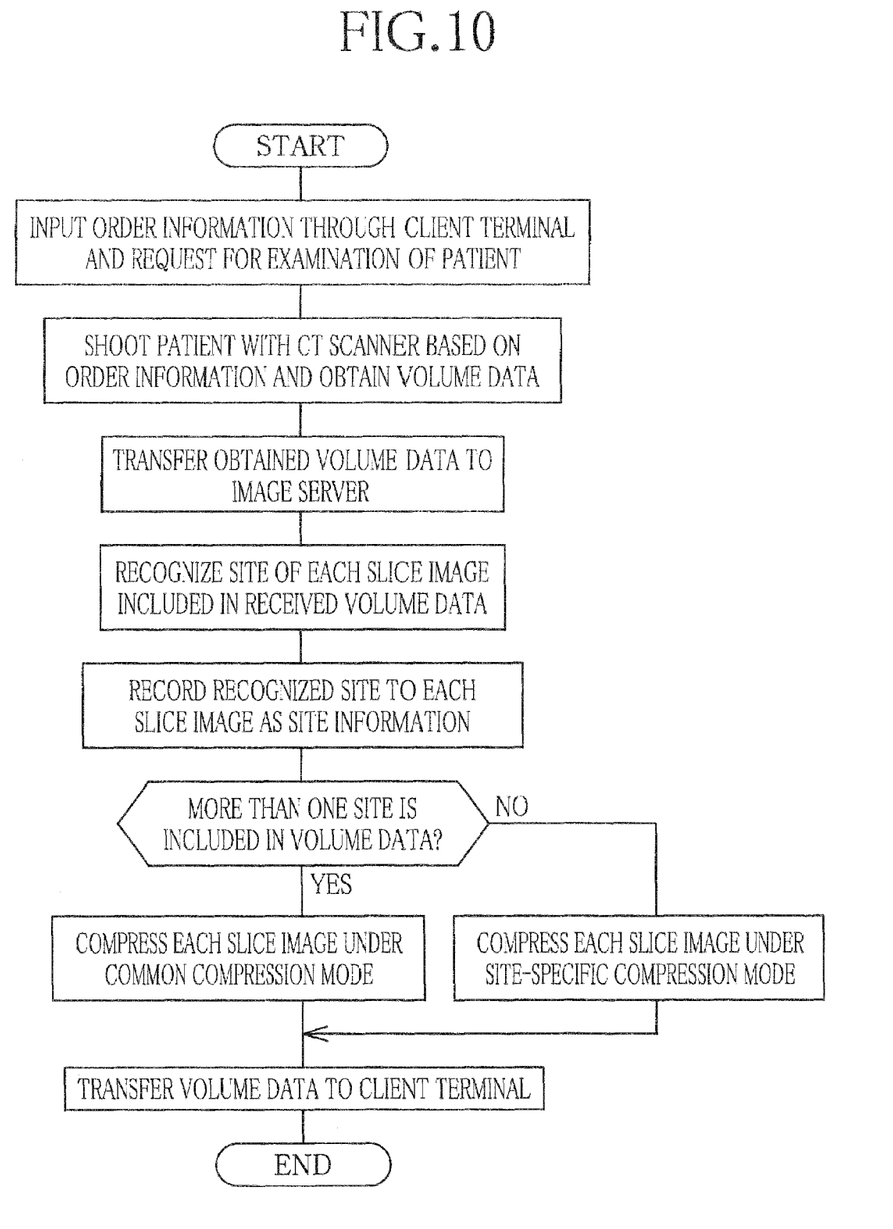
FIG. 10 is a flow chart showing an example of transferring data after the compression of the data.

In the above embodiment, although the volume data 32 is stored in the HDD 42 after the compression is performed to the respective slice images 30, the volume data 32 may instead be transferred to the client terminal 18 after the compression as shown in the flow chart of FIG. 10. At this time, the volume data 32 may be transferred to the client terminal 18 that requested the shooting of the volume data 32 or to the client terminal 18 in the department specializing in the site being shot. In addition, when more than one site is included in the volume data 32, the slice images 30 included in the volume data 32 may be classified by site and respectively sent to the specializing department.

In the above embodiment, compression is performed when the image server 14 receives the volume data 32 from the CT scanner 12. However, the timing for performing compression is not limited to this. For example, the volume data 32 may be stored in the image server 14 without performing compression thereto, and compression may be performed when it is requested to be transferred to the client terminal 18. It is also possible to provide the CT scanner 12 with a compression section so that the compressed image is sent to the image server 14.

Figure 11:
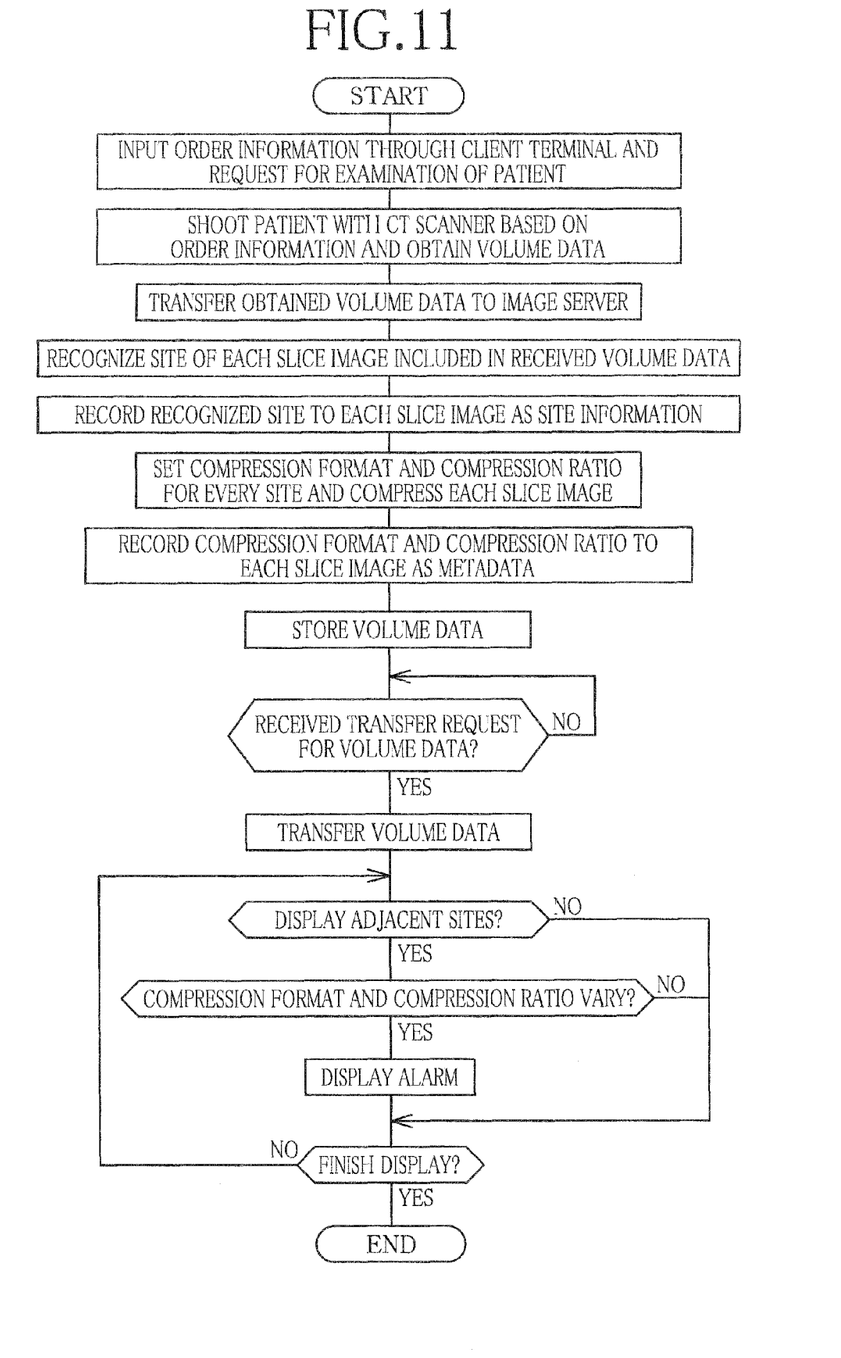
FIG. 11 is a flow chart showing an example of displaying the alarm display instead of changing the compression mode.

In the above embodiment, although the compression mode is set based on whether plural sites are included in the volume data 32 or not, the present invention is not limited to this, but may be set in the way shown in the flow chart of FIG. 11. In the flow chart of FIG. 11, after the site information 36c is formed by the site recognition, the compression format and the compression ratio are set for each site and compression is performed to the respective slice images 30. That is, the image compression section 47 is made to perform compression under the site-specific compression mode at any time regardless of whether plural sites are included in the volume data 32 or not.

After the compression by the image compression section 47, the CPU 40 records the compression format and the compression ratio set for each slice image 30 as meatadata to the tag area 36 of the slice image 30. After recording the compression format and the compression ratio, the CPU 40 stores the compressed volume data 32 to the HDD 42.

Upon receipt of the transfer request of the volume data 32 from the client terminal 18, the CPU 40 reads out the requested volume data 32 from the HDD 42 and transfers it to the client terminal 18 which has requested. The client terminal 18 that received the volume data 32 displays the slice images 30 included in the volume data 32 on the monitor 22. At this time, the client terminal 18 refers to the site information 36c of each slice image 30 and judges whether more than one site is included in a group of slice images displayed on the monitor 22 simultaneously or continuously.

When judging as more than one site is included, the client terminal 18 refers to the compression format and the compression ratio recorded as the metadata in each slice image 30 and judges whether different compression format and compression ratio are used between the adjacent sites or not. When judging as different compression format and compression ratio are used between the adjacent sites, the client terminal 18 displays an alarm message on the monitor 22 and notifies the user that different compression format and compression ratio are used between the adjacent sites. Owing to such alarm display, the user can be notified, and thereby preventing misdiagnosis due to image quality change between the adjacent sites.

In the above embodiment, although the recognition of the site being shot in each slice image 30 is automatically made by the image analysis, the present invention is not limited to this. The site recognition may be made by the doctor's observation. When the site recognition is made by the observation, the doctor or the like may manually record the site information 36c.

In the above embodiment, although the site information 36c is recorded in the tag area 36 of the slice image 30 as the metadata, the present invention is not limited to this. For example, a tabular file in which the slice images 30 and the sites are associated with each other is prepared, and the site information 36c of the respective slice images 30 may be recorded altogether. Moreover, in the above embodiment, although the compression format and the compression ratio are set when compression is performed, the present invention is not limited to this. For example, either the compression format or the compression ratio may be set or other categories may also be added.

In the above embodiment, although the slice image 30 shot with the CT scanner 12 is used as the medical image, the present invention is not limited to this. For example, those shot with other modalities like the MRI scanner or the PET scanner may also be used as the medical image.

In the above embodiment, the present invention is applied to the medical network system 10 used in one medical facility. However, the present invention may also be applied to, for example, a medical network system in which more than one medical facility is interconnected. Moreover, although the image server 14 is shown as the image compression device, the present invention is also applicable in a case where, for example, the client terminal 18 is used as the image compression device.

INDUSTRIAL APPLICABILITY

The present invention is utilized for compressing medical images obtained through a single examination.

The invention claimed is:

1. An image compression method for selecting a compression mode and performing compression to an image group of more than one medical image shot with a modality, said compression method comprising:
   a judgment step of judging whether or not more than one anatomical site is included in said image group based on site information indicating anatomical site of each said medical image; and
   a compression step of performing compression
   i) under a common compression mode when it is judged that more than one anatomical site is included in said image group, and
   ii) under a site-specific compression mode when it is judged that only one anatomical site is included in said image group, wherein,
   i) the site-specific compression mode uses at least one of a) a compression format, and b) a compression ratio corresponding to an anatomical site, and
   ii) the common compression mode uses at least one of a) a common compression format, and b) a common compression ratio regardless of said anatomical site.

2. The image compression method of claim 1, wherein under said site-specific compression mode, compression information indicating a compression format and a compression ratio for each anatomical site is referred, and the compression format and/or the compression ratio corresponding to said anatomical site is set.

3. The image compression method of claim 1, further comprising:
   a site recognition step of recognizing an anatomical site in said medical image by image analysis before said judgment step; and
   a site information production step of producing said site information regarding each said medical image based on the recognition result of said site recognition step.

4. The image compression method of claim 1, wherein said site information is recorded in each said medical image as metadata.

5. The image compression method of claim 1, further comprising:
   a storage step of storing said image group after said compression to a storage means.

6. The image compression method of claim 1, further comprising:
   a transfer step of transferring said image group after said compression to a terminal used for a diagnosis.

7. The image compression method of claim 1, wherein said anatomical site is at least one of head, neck, chest, abdomen, pelvic region and leg.

8. The image compression method of claim 1, wherein said medical image is a slice image capturing cross section of a human body.

9. An image compression device for selecting a compression mode and performing compression to an image group of more than one medical image shot with a modality, said compression device comprising:
   a judgment means for judging whether or not more than one anatomical site is included in said image group based on site information indicating anatomical site of each said medical image; and
   a compression means for performing compression
   i) under a common compression mode when it is judged that more than one anatomical site is included in said image group, and
   ii) under a site-specific compression mode when it is judged that only one anatomical site is included in said image group, wherein,
   i) the site-specific compression mode uses at least one of a) a compression format, and b) a compression ratio corresponding to an anatomical site, and
   ii) the common compression mode uses at least one of a) a common compression format, and b) a common compression ratio regardless of said anatomical site.

10. A medical network system, comprising:
    a server;
    a terminal connected to said server through a network,
    said server having a storage unit storing an image group of more than one medical image shot with a modality, each said medical image including site information indicating an anatomical site of said medical image,
    wherein said server is configured to select one of
    i) a site-specific compression mode using one of
       a) a compression format, and
       b) a compression ratio corresponding to an anatomical site, and
    ii) a common compression mode using one of
       a) a common compression format, and
       b) a common compression ratio regardless of said anatomical site, and
    wherein said server is configured to, based on said selected compression mode, perform compression to said image group, and
    wherein said server is configured so that said image group is read out from said server to said terminal upon request from a user;
    a judgment unit configured to judge whether or not more than one anatomical site is included in said image group based on the site information indicating the anatomical site of each said medical image; and
    a compression unit configured to perform compression
    i) under said common compression mode when the judgment unit judges that more than one anatomical site is included in said image group, and
    ii) under said site-specific compression mode when the judgment unit judges that only one anatomical site is included in said image group.

* * * * *